United States Patent
Fukutomi

(10) Patent No.: US 6,913,459 B2
(45) Date of Patent: Jul. 5, 2005

(54) ORTHODONTIC BRACKET

(75) Inventor: Hitoshi Fukutomi, Fukushima (JP)

(73) Assignee: Tomy Incorporated, Fukushima (JP)

( * ) Notice: Subject to any disclaimer, the term of this patent is extended or adjusted under 35 U.S.C. 154(b) by 198 days.

(21) Appl. No.: 10/260,305

(22) Filed: Oct. 1, 2002

(65) Prior Publication Data

US 2003/0064342 A1 Apr. 3, 2003

(30) Foreign Application Priority Data

Oct. 1, 2001 (JP) .................................. P.2001-304900

(51) Int. Cl.[7] .............................................. A61C 3/00
(52) U.S. Cl. .............................................. 433/8; 433/10
(58) Field of Search .................... 433/8, 9, 10, 11, 433/12, 13, 14, 15, 16, 17

(56) References Cited

U.S. PATENT DOCUMENTS 4,302,532 A * 11/1981 Wallshein .................... 433/8
6,264,469 B1 * 7/2001 Moschik ...................... 433/8

* cited by examiner

Primary Examiner—Cary E. O'Connor
Assistant Examiner—Candice C. Stokes
(74) Attorney, Agent, or Firm—Sughrue Mion, PLLC

(57) ABSTRACT

An orthodontic bracket 10 is a plastic bracket, having a base 11 directly or indirectly secured to the teeth, a bracket main body 12 furnished on the base 11 at its one side, an archwire slot 16 formed in groove shape along a mesiodistal direction with respect to the bracket main body 12 for receiving an archwire 14, and a liner 20 of U-shape in cross section provided along the archwire slot 16. This orthodontic bracket 10 is furnished with flared portions 22A, 22B at outsides of the liner 20, and the flared portions 22A, 22B are composed not to project from the surfaces 13A, 13B of the bracket main body 12.

15 Claims, 5 Drawing Sheets

ORTHODONTIC BRACKET

BACKGROUND OF THE INVENTION

The present invention relates to an orthodontic bracket, and in particular an orthodontic bracket where a liner is provided in an archwire slot for receiving an archwire so as to increase rupture strength and sliding property of the archwire slot.

For example, among conventional orthodontic brackets, some comprise a plate-shaped base to be secured to the surface of the teeth, a bracket main body furnished on the base at its one side, an archwire slot formed in the bracket main body, and a liner of U-shape in cross section provided along the archwire slot.

The liner is provided in the archwire slot, thereby enabling to reinforce the archwire slot. For correcting a bad row of teeth, a square or rectangular archwire is received within the liner following a sequence of the archwire, so that the archwire slot can be avoided from bending with the liner when applying torque to the archwire slot through the square or rectangular archwire.

Sliding property within the archwire slot can be improved by the liner. In case a bracket main body is composed of ceramics or plastic, the sliding with the archwire is inferior as known, and for example, if a metal-made liner is furnished, friction with the archwire can be reduced.

One example is known as a liner shown in FIG. 8. The liner 100 is defined with respective openings 102 in both side walls 101, and when the liner 100 is inserted in the orthodontic bracket, plastic flows into each of the openings 102 to prevent the liner 100 from slipping out of the orthodontic bracket.

Another example is known as a liner shown in FIG. 9. The liner 105 is formed with projections 107 in both side walls 106 toward a mesiodistal direction, and when the liner 105 is inserted in the orthodontic bracket, plastic flows into each of under-cut portions 108 under the projections 107 to prevent the liner 105 from slipping out of the orthodontic bracket.

A further example is known as a liner shown in FIG. 10. The liner 110 is provided with flanges 111 bent at right angle at mesiodistal ends, and the flanges 111 prevent the liner 110 from slipping out of the orthodontic bracket.

A still further example is known as a liner shown in FIG. 11. The liner 115 extends white-coated wings 116 to the inside of tiewings of the orthodontic bracket, and the wings 116 prevent the liner 115 from slipping out of the orthodontic bracket.

A yet further example is known as a liner shown in FIG. 12. The liner 120 is formed with bulky parts 121, and when the liner 120 is inserted in the orthodontic bracket, the respective bulky parts 121 are buried in the plastic to prevent the liner 120 from slipping out of the orthodontic bracket.

However, as to the liner 100 shown in FIG. 8, if the plastic too much projects from the respective openings 102, the projected plastic obstructs the archwire sliding and causes delay in curing for the correction of dentition. Therefore, it is necessary to heighten precision when the liner 100 is inserted into the orthodontic bracket, and this hampers the cost-down.

Further, as to the liner 105 shown in FIG. 9, if the plastic too much goes out from the respective under-cut parts 108, the projected plastic obstructs the archwire sliding and consequently causes delays of movement of the teeth. Therefore, similarly to the liner 100 of FIG. 8, it is necessary to heighten precision when the liner 105 is inserted into the orthodontic bracket, and this hampers the cost-down.

In addition, the liner 110 shown in FIG. 10 is provided with the respective flanges 111 bent at the mesiodistal ends, and when the liner 110 is inserted into the orthodontic bracket, the flanges 111 project from the mesiodistal ends of the orthodontic bracket, so that there is a room for improving an external appearance.

In the liner shown in FIG. 11, even if the wings 116 is white-coated but as it extends to the inside of the transparent plastic tiewings, a room is still left for improving the external appearance.

Besides, since the liner 120 shown in FIG. 12 is formed with the bulky parts 121, it is complicated in shape, and it is difficult to maintain the liner precise, and this disturbs the cost-down.

SUMMARY OF THE INVENTION

The invention has been realized in view of the above mentioned problems, and it is an object of the invention to provide an orthodontic bracket maintaining rupture strength of the archwire slot, while restraining the cost and heightening the external appearance.

For accomplishing the above mentioned object, an orthodontic bracket, according to a first aspect of the present invention including a base directly or indirectly secured to the teeth, a bracket main body furnished on the base at its one side, an archwire slot formed in groove shape in a mesiodistal direction with respect to the bracket main body for receiving an archwire, and a liner of U-shape in cross section provided along the archwire slot. In the orthodontic bracket of the present invention, flared portions are furnished at outsides of the liner, and the flared portions do not project from the surface of the bracket main body. In other words, the liner has a length substantially equal or less than a length of the bracket main body in the mesiodistal direction.

The thus structured orthodontic bracket has flared portions at the outsides of the liner, and the flared portions do not project from the surface of the bracket main body, so that the flared portions are securely buried in the bracket main body for preventing the liner from getting out of the bracket main body.

As the flared portions do not project from the surface of the bracket main body, those are hidden within the bracket main body, thereby to heighten the external appearance.

Further, the flared portion plays a role of guiding the archwire into the archwire slot for making insertion of the archwire easy.

The above-mentioned object can also be achieved by an orthodontic present invention, including a base directly or indirectly secured to the teeth, a bracket main body furnished on the base at its one side, an archwire slot formed in groove shape in a mesiodistal direction with respect to the bracket main body for receiving an archwire, and a liner of U-shape in cross section provided along the archwire slot. In the orthodontic bracket, the liner is rugged allover the outside face thereof.

The liner is rugged allover the outside face thereof, thereby enabling to firmly attach the liner to the bracket main body only by contacting the bracket main body with the thus rugged outside face and avoid the liner from slipping out of the bracket main body. A work of inserting the liner into the bracket main body is made easy thereby.

In the above-mentioned orthodontic bracket according to the present inventions, it is advantageous that the outside is furnished allover with a mesh material, thereby to be rugged.

The outside of the liner is furnished allover with the mesh material, thereby to be rugged, so that the ruggedness is easily formed. Further, in the above-mentioned orthodontic bracket according to the present inventions, it is advantageous that the outside is performed allover with an etching process, thereby to be rugged, so that the ruggedness is easily formed.

DETAILED DESCRIPTION OF THE PREFERRED EMBODIMENTS

In the following description, embodiments of the invention will be explained with reference to the attached drawings. In each of the embodiments, as to the members and others having already been explained in FIG. 1, explanations will be simplified or omitted by giving the same or corresponding references.

Figure 1:
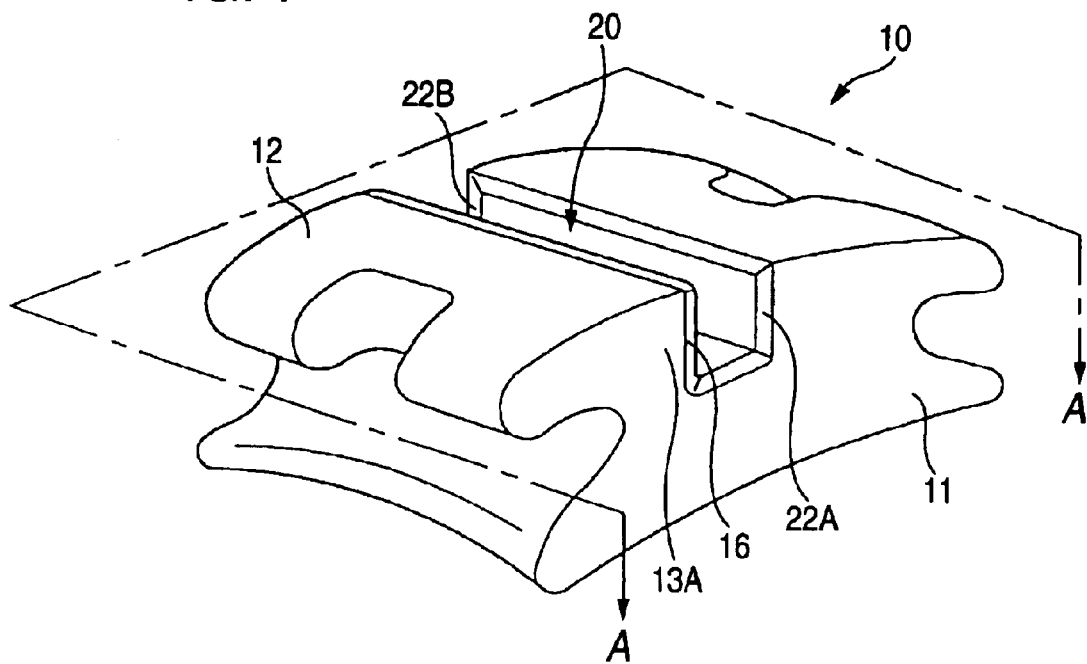
FIG. 1 is a perspective view showing the first embodiment of the orthodontic bracket according to the invention.
Figure 2:
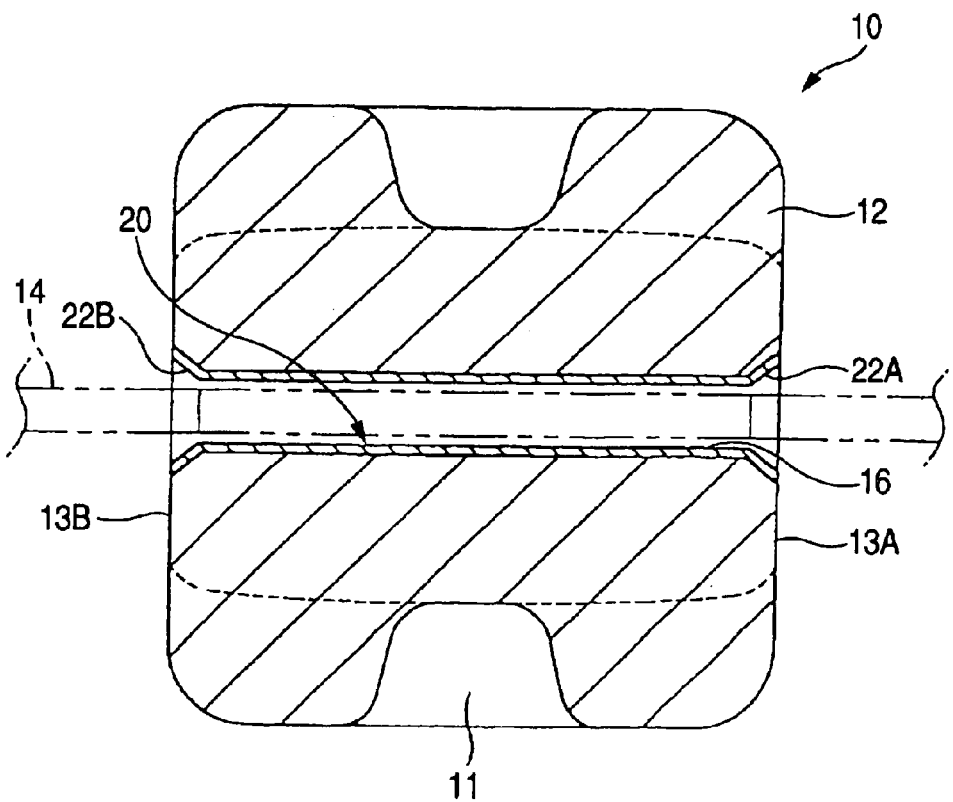
FIG. 2 is a cross sectional view taken along A—A line of FIG. 1.

As shown in FIGS. 1 and 2, the orthodontic bracket 10 as a first embodiment of the invention, is a plastic bracket, having a base 11 directly or indirectly secured to the teeth, a bracket main body 12 furnished on the base 11 at its one side, an archwire slot formed in groove shape in a mesiodistal direction with respect to the bracket main body 12 for receiving an archwire 14 (as one example, a squire wire), and a liner 20 of U-shape in cross section provided along the archwire slot 16.

This orthodontic bracket 10 is so composed that the flared portions 22A, 22B are furnished at the outside (the parts of the mesiodistal direction) of the liner 20, and the flared portions 22A, 22B do not project from the surface (the parts of the mesiodistal direction) of the bracket main body.

The liner 20 is inserted when the bracket main body 12 is, e.g., injected.

The flared portions 22A, 22B are furnished at the outsides (the parts of the mesiodistal direction) of the liner 20, and are buried in the bracket main body 12, whereby the liner 20 is prevented from sliding in the mesiodistal direction with respect to the bracket main body 12.

Further, the flared portions 22A, 22B are buried not to project from the surface 13A, 13B (the parts of the mesiodistal direction) of the bracket 12, thereby to increase the outer appearance of the orthodontic bracket 10.

Figure 3:
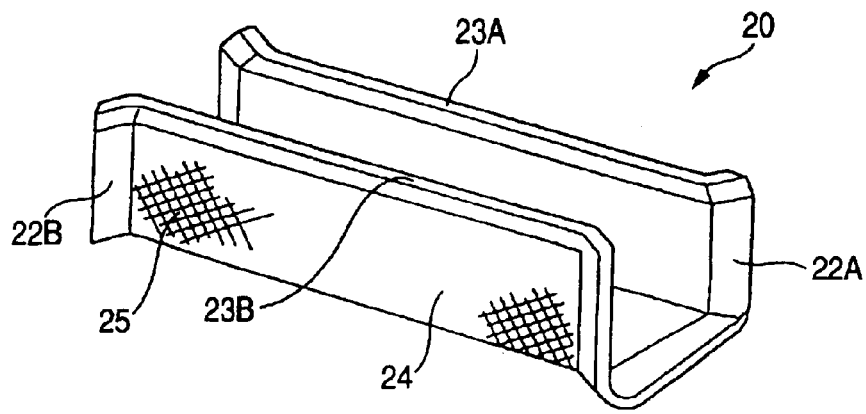
FIG. 3 is a perspective view showing the liner used in the first embodiment according to the invention.
Figure 4:
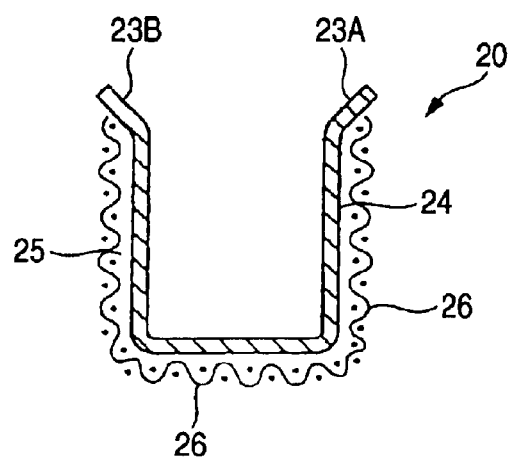
FIG. 4 is a perspective view showing the liner used in the first embodiment according to the invention.

As seen in FIGS. 3 and 4, the liner 20 bends in taper outside a pair of the upper sides (called as "upper flared portions" hereafter) 23A, 23B, and bends in taper outside the flared portions 22A, 22B provided at the outer sides (the parts of the mesiodistal direction).

The liner 20 bends in an outer shape taper the pair of upper flared portions, whereby the archwire 14 can be more smoothly received in the liner 20.

In addition, the flared portions 22A, 22B are bent in an outer taper shape, thereby to reinforce the liner 20. When the square or rectangular archwire 14 is inserted in the liner 20 and torque is added, the upper flared portions 23A, 23B (that is, the liner 20) may be prevented from opening.

Besides, the flared portions 22A, 22B are bent outward, so that sliding of the archwire 14 is made better to reduce friction of the liner 20.

The outside 24 of the liner 20 is furnished allover with the mesh material 25, thereby to be rugged. Thus, the outside 24 of the liner 20 is furnished allover with the ruggedness 26, thereby enabling to prevent the liner 20 from slipping out of the bracket main body 12 only by contacting the bracket main body 12 along the ruggedness 26.

The work of inserting the liner 20 into the bracket main body 12 is made easy thereby. The outside 24 of the liner 20 is furnished allover with the mesh material 25, thereby to be rugged 25, so that the ruggedness 26 is easily formed.

Next, a second embodiment will be explained.

Figure 5:
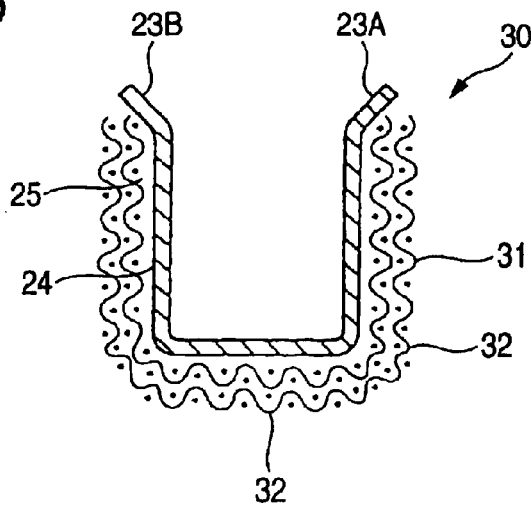
FIG. 5 is a cross sectional view showing the second embodiment according to the invention.

The liner 30 as the second embodiment of the invention shown in FIG. 5 is formed with the ruggedness 32 by furnishing an external mesh member 31 allover a mesh member 25 of the liner 20. Thus, the external mesh member 31 is furnished allover the outside 24 of the mesh member 25, thereby enabling to make the mesh member 25 fine and the external mesh member 31 rough.

By making the mesh member 25 fine, the mesh member 25 may be furnished in the liner 20 under a condition of being more fitted. In addition, by making the external mesh member 31 rough, the external mesh member 31 may be more securely fixed to the bracket main body 12. The liner 20 can be more surely prevented from slipping out of the bracket main body 12.

A third embodiment will be explained.

Figure 6:
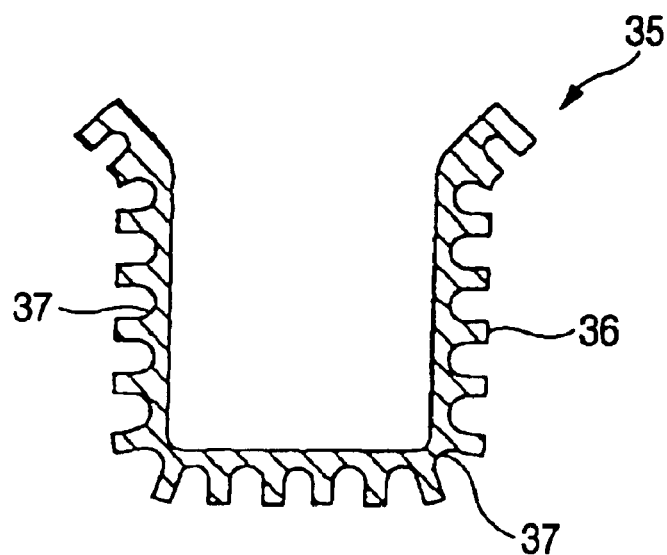
FIG. 6 is a cross sectional view showing the third embodiment according to the invention.

The liner 35 as the third embodiment of the invention shown in FIG. 6 is formed with the ruggedness 37 by carrying out an etching process allover the outside 36. The liner 35 and other structure are the same as those of the first embodiment.

The liner 35 is formed with the ruggedness 37 allover the outside 36, thereby enabling to avoid the liner 35 from slipping out of the bracket main body 12 only by contacting the bracket main body 12 along the ruggedness 37.

The work of inserting the liner 35 into the bracket main body 12 is made easy thereby. Thus, the outside 36 of the liner 35 is carried out allover with the etching process to form the ruggedness 36.

A fourth embodiment will be explained.

Figure 7:
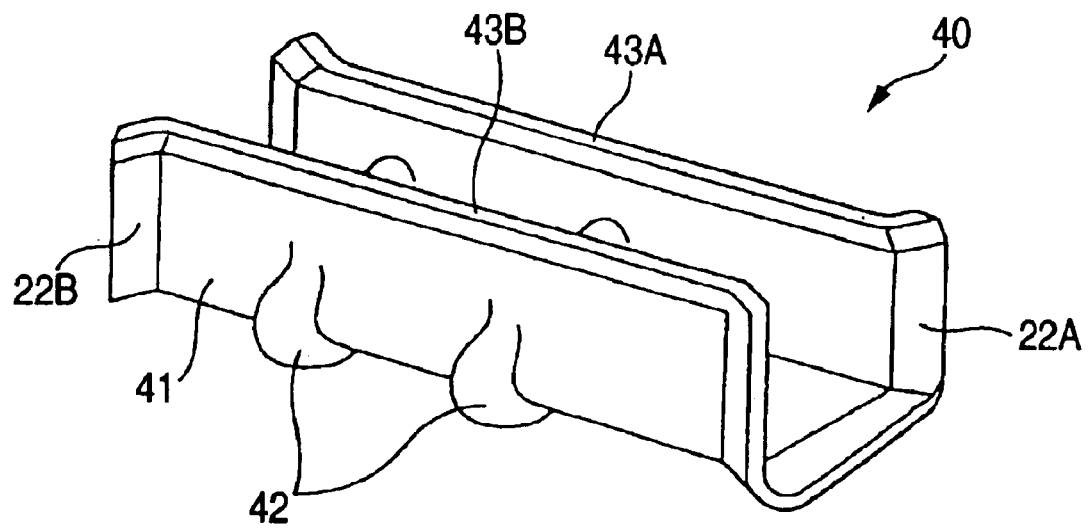
FIG. 7 is a cross sectional view showing the fourth embodiment according to the invention.
Figure 8:
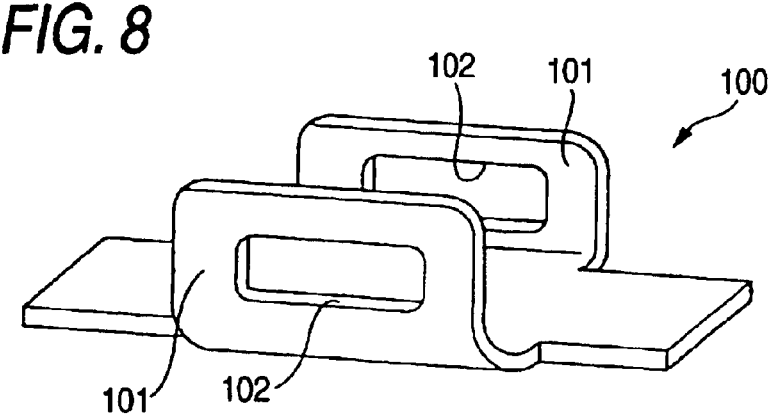
FIG. 8 is a perspective view showing the conventional liner for the bracket main body.
Figure 9:
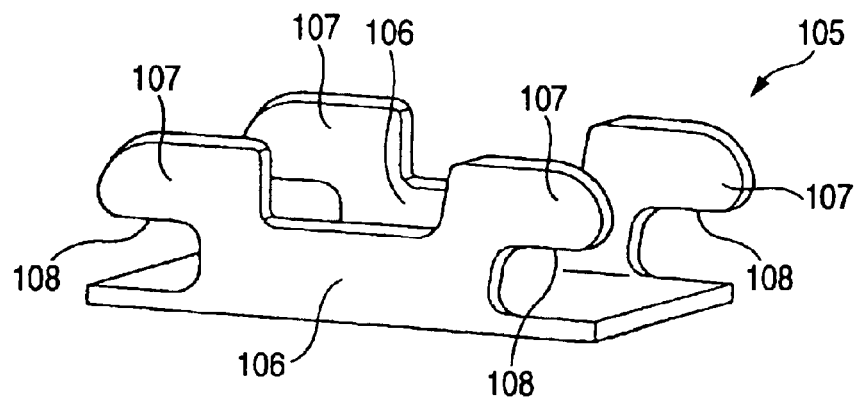
FIG. 9 is a perspective view showing another conventional liner for the bracket main body.
Figure 10:
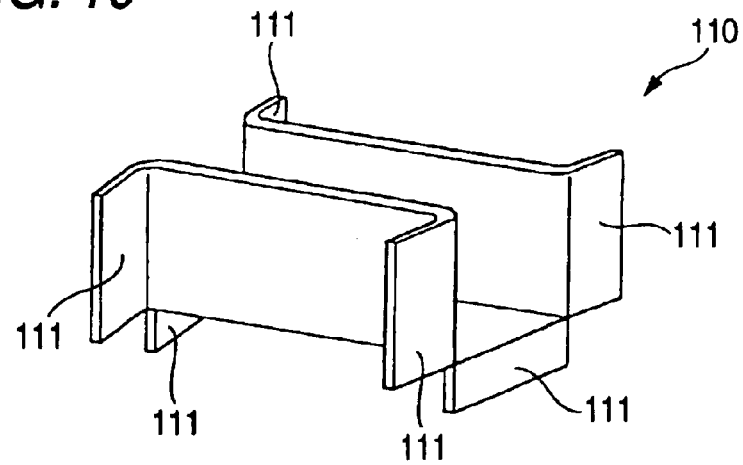
FIG. 10 is a perspective view showing a further conventional liner for the bracket main body.
Figure 11:
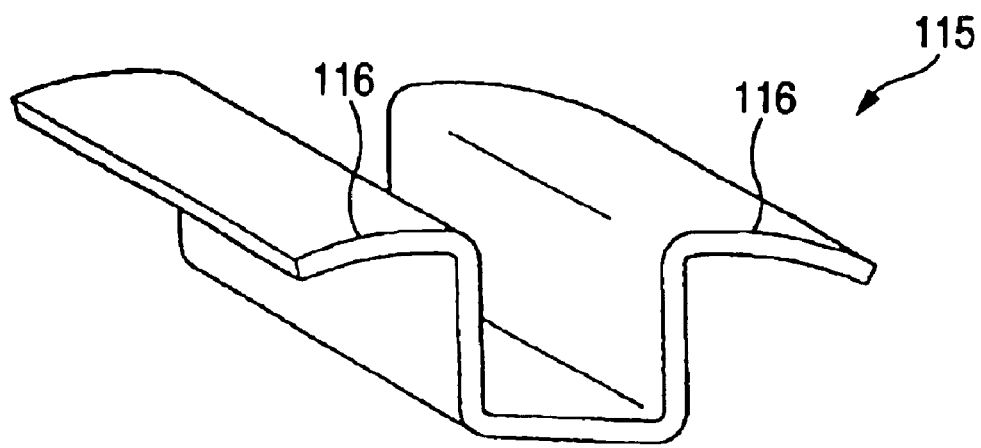
FIG. 11 is a perspective view showing a still further conventional liner for the bracket main body.
Figure 12:
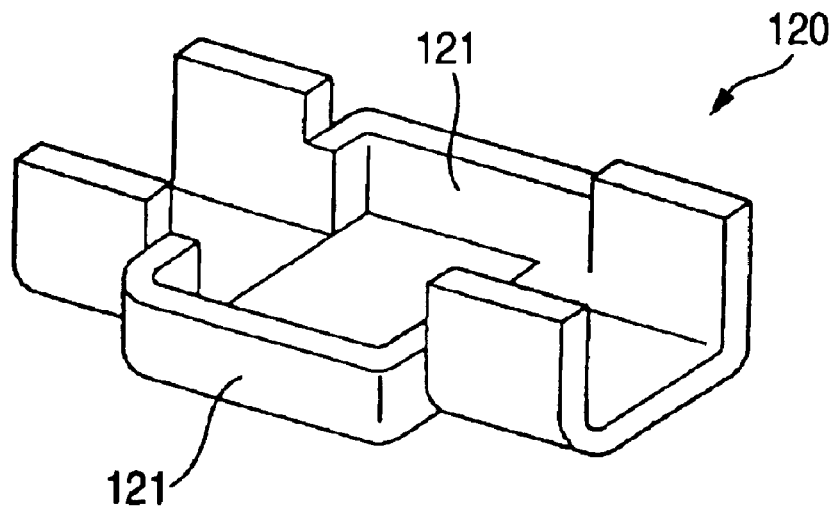
FIG. 12 is a perspective view showing a yet further conventional liner for the bracket main body.

The liner 40 as the fourth embodiment of the invention shown in FIG. 7 is formed with portions 42 expanded outside (called as "beads" hereafter) at a plurality of parts (as one example, two parts). The liner 40 and other structure are the same as those of the first embodiment.

The liner 40 is formed with the beads 42 at the outside 41 of the liner 40, thereby enabling to avoid the liner 40 from slipping out of the bracket main body 12 only by contacting the bracket main body 12 along the beads 42.

The work of inserting the liner 40 into the bracket main body 12 is made easy thereby. In addition, the liner 40 bends in taper outside the flared portions 22A, 22B, and the beads 42 are formed at the outside 41, thereby more reinforcing the liner 40. Thus, when the archwire 14 (as one example, the square wire) is inserted in the liner 40 and the torque is effected thereto, the upper flared portions 43A, 43B (that is, the liner 40) can be exactly avoided from opening.

The above mentioned embodiments have been explained as to the orthodontic bracket by use of the examples of the plastic bracket, but no limitation is made only thereto, and it is possible to apply to the ceramic bracket or the glass bracket.

In this case, since the liner cannot be inserted as the plastic bracket, the liner is attached to the ceramic bracket or the glass bracket by an adhesive or brazing.

The orthodontic bracket of the invention are not limited to the above mentioned respective embodiments, but appropriate modifications or improvements are available.

As far as accomplishing the invention, no limitation is made to material quality, shapes, dimensions, forms, number of the orthodontic bracket, base, bracket main body, liners exemplified in the respective embodiments.

As explained above, according to the present invention, as set forth in the first aspect thereof, the liner is furnished outside with the flared portions which are buried in the bracket main body. Thereby, the liner can be avoided from slipping out of the bracket main body, so that the liner reinforces the archwire slot to prevent breakage.

The flared portion does not project from the surface of the bracket main body, thereby to improve the external appearance of the orthodontic bracket.

As the liner reinforces the archwire slot and heightens the external appearance, the quality of the orthodontic bracket can be improved.

According to the present invention, as set forth in the second aspect thereof, the liner is rugged allover the outside face thereof, thereby enabling to avoid the liner from slipping out of the bracket main body only by contacting the bracket main body along the ruggedness. The work of inserting the liner 35 into the bracket main body 12 is made easy thereby, and the cost of the orthodontic bracket can be suppressed.

Further, according to the present invention, the outside of the liner is performed allover with the mesh member, thereby to be rugged, so that the ruggedness is easily formed and the cost of the liner can be suppressed.

In addition, according to the present invention, the outside is performed allover with the etching process, thereby to be rugged, so that the ruggedness is easily formed and the cost of the liner can be suppressed.

While there has been described in connection with the preferred embodiments of the invention, it will be obvious to those skilled in the art that various changes and modifications may be made therein without departing from the invention, and it is aimed, therefore, to cover in the appended claims all such changes and modifications as fall within the true spirit and scope of the invention.

What is claimed is:

1. An orthodontic bracket comprising:
a base directly or indirectly secured to the teeth;
a bracket main body provided on one side of the base;
an archwire slot formed into a groove shape extending in a mesiodistal direction with respect to the bracket main body for receiving an archwire therein; and
a liner having a U-shape cross section and being provided along the archwire slot, said liner including flared portions that are formed at its edge portions in the mesiodistal direction, and upper flared portions that are formed at its upper edges, wherein the liner has a length substantially equal or less than a length of the bracket main body in the mesiodistal direction in such a manner that the flared portions do not project from side surfaces of the bracket main body.

2. The orthodontic bracket as set forth in claim 1, wherein the liner has an outside uneven surface which is engaged with the bracket main body.

3. An orthodontic bracket, comprising:
a base directly or indirectly secured to the teeth;
a bracket main body provided on one side of the base:
an archwire slot formed into a groove shape extending in a mesiodistal direction with respect to the bracket main body for receiving an archwire therein; and
a liner having a U-shape cross section and being provided along the archwire slot, said liner including flared portions that are formed at its edge portions in the mesiodistal direction, wherein the liner has a length substantially equal or less than a length of the bracket main body in the mesiodistal direction in such a manner that the flared portions do not project from side surfaces of the bracket main body,
wherein the liner has an outside uneven surface which is engaged with the bracket main body, and
wherein the outside uneven surface is formed with a mesh member to be attached to the liner.

4. The orthodontic bracket as set forth in claim 3, wherein the mesh member comprises:
an external mesh; and
an internal mesh having a mesh size finer than the external mesh.

5. The orthodontic bracket as set forth in claim 2, wherein the outside uneven surface is formed all surfaces between the flared portions in the mesiodistal direction.

6. The orthodontic bracket as set forth in claim 2, wherein the outside uneven surface is formed by an etching process.

7. The orthodontic bracket as set forth in claim 6, wherein the outside uneven surface is formed on all surfaces between the flared portions in the mesiodistal direction.

8. An orthodontic bracket, comprising:
a base directly or indirectly secured to the teeth;
a bracket main body provided on one side of the base;
an archwire slot formed into a groove shape extending in a mesiodistal direction with respect to the bracket main body for receiving an archwire therein; and
a liner having a U-shape cross section and being provided along the archwire slot, said liner including flared portions that are formed at its edge portions in the mesiodistal direction, wherein the liner has a length substantially equal or less than a length of the bracket main body in the mesiodistal direction in such a manner that the flared portions do not project from side surfaces of the bracket main body, wherein the liner has an outside uneven surface which is engaged with the bracket main body, and wherein the outside uneven surface has at least one bead portion.

9. An orthodontic bracket comprising:

a base directly or indirectly secured to the teeth;

a bracket main body provided on one side of the base;

an archwire slot formed into a groove shape extending in a mesiodistal direction with respect to the bracket main body for receiving an archwire therein; and a liner having a U-shape cross section and being provided along the archwire slot, said liner including an outside uneven surface which is engaged with the bracket main body, wherein said liner includes upper flared portions on upper edges of the liner.

10. An orthodontic bracket, comprising:

a base directly or indirectly secured to the teeth;

a bracket main body provided on one side of the base;

an archwire slot formed into a groove share extending in a mesiodistal direction with respect to the bracket main body for receiving an archwire therein; and a liner having a U-shape cross section and being provided along the archwire slot, said liner including an outside uneven surface which is engaged with the bracket main body, wherein the outside uneven surface is formed with a mesh member to be attached to the liner.

11. The orthodontic bracket as set forth in claim 10, wherein the mesh member comprises:

an external mesh; and an internal mesh having a mesh size finer than the external mesh.

12. The orthodontic bracket as set forth in claim 9, wherein said liner includes flared portions that are formed at its edge portions in the mesiodistal direction, and the outside uneven surface is formed on all surfaces between the flared portions in the mesiodistal direction.

13. The orthodontic bracket as set forth in claim 9, wherein the outside uneven surface is formed by an etching process.

14. The orthodontic bracket as set forth in claim 13, wherein said liner includes flared portions that are formed at its edge portions in the mesiodistal direction, and the outside uneven surface is formed over all surfaces between the flared portions in the mesiodistal direction.

15. An orthodontic bracket, comprising:

a base directly or indirectly secured to the teeth;

a bracket main body provided on one side of the base;

an archwire slot formed into a groove shape extending in a mesiodistal direction with respect to the bracket main body for receiving an archwire therein; and a liner having a U-shape cross section and being provided along the archwire slot, said liner including an outside uneven surface which is engaged with the bracket main body, wherein the outside uneven surface has at least one bead portion.

* * * * *